United States Patent
Keppler

(10) Patent No.: US 8,362,266 B2
(45) Date of Patent: Jan. 29, 2013

(54) METHOD OF MANUFACTURING A RUTHENIUM COMPLEX

(75) Inventor: Berhhard Keppler, Hockenheim (DE)

(73) Assignee: Niiki Pharma Inc., Hoboken, NJ (US)

( * ) Notice: Subject to any disclaimer, the term of this patent is extended or adjusted under 35 U.S.C. 154(b) by 642 days.

(21) Appl. No.: 12/636,025

(22) Filed: Dec. 11, 2009

(65) Prior Publication Data

US 2010/0094019 A1    Apr. 15, 2010

Related U.S. Application Data

(63) Continuation of application No. PCT/US2008/066456, filed on Jun. 10, 2008.

(60) Provisional application No. 60/943,283, filed on Jun. 11, 2007.

(51) Int. Cl.
*C07F 15/00*    (2006.01)
(52) U.S. Cl. ........................................... 548/108
(58) Field of Classification Search ........... 548/108
See application file for complete search history.

(56) References Cited

U.S. PATENT DOCUMENTS

| 4,843,069 A | 6/1989 | Keppler et al. |
| 2005/0032801 A1 | 2/2005 | Keppler |

FOREIGN PATENT DOCUMENTS

WO    9736595    10/1997

OTHER PUBLICATIONS

Kapitza, et al., "Heterocyclic Complexes of Ruthenium(III) Induce Apoptosis in Colorectal Carcinoma Cells," J. Cancer Res. Clin. Oncol. 131:101-110 (2005).

Peti, W., et al., "Synthesis of Tumor-Inhibiting Complex Salts Containing the Anion Trans Tetrachlorobis(Indazole) Ruthenate(III) and Crystal Structure of the Tetraphenyl-Phosphonium Salt," Eur. J. Inorg. Chem. 1551-1555(1999).

United States Patent and Trademark Office, Combined International Search Report and Written Opinion for PCT/US2008/066456, dated Sep. 8, 2008.

*Primary Examiner* — Jason M Nolan

(74) *Attorney, Agent, or Firm* — Jun He Law Offices P.C.; James J. Zhu; Jay Z. Zhang

(57) ABSTRACT

A method of making an alkali metal salt of trans-[tetrachlorobis(1H-indazole)ruthenate (III)] is disclosed.

5 Claims, No Drawings

METHOD OF MANUFACTURING A RUTHENIUM COMPLEX

CROSS-REFERENCE TO RELATED APPLICATION

This application is a Continuation of International Application Number PCT/US2008/066456 filed Jun. 10, 2008, and designating the United States, which claims priority to U.S. Provisional Application No. 60/943,283 filed Jun. 11, 2007, both of which are incorporated herein by reference in their entirety.

FIELD OF THE INVENTION

This invention generally relates to chemical synthesis, and particularly relates to a method of making an alkali metal salt of trans-[tetrachlorobis(1H-indazole)ruthenate (III)].

BACKGROUND OF THE INVENTION

A number of ruthenate compounds are known in the art to be useful as anti-tumor compounds. See e.g., U.S. Pat. No. 4,843,069, PCT Publication No. WO 9736595, and US Application Publication No. 2005032801. In particular, the compounds ruthenium complex salt indazolium trans-[tetrachlorobis(1H-indazole)ruthenate (III)] (KP1099) and sodium trans-[tetrachlorobis(1H-indazole)ruthenate (III)] (KP1339) have been shown to be highly potent in inducing apoptosis in a broad spectrum of cancer cells. See e.g., Kapitza et al., *J. Cancer Res. Clin. Oncol.*, 131(2):101-10 (2005).

The existing methods of making sodium trans-[tetrachlorobis(1H-indazole)ruthenate (III)] (KP1339) in the art are cumbersome. For example, W. Peti et al, *Eur. J. Inorg. Chem.* 1999, 1551-1555 discloses the following synthesis scheme.

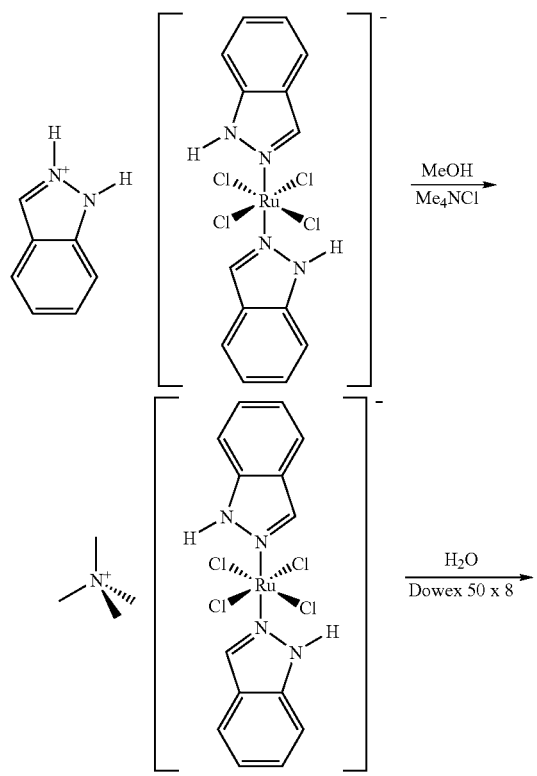

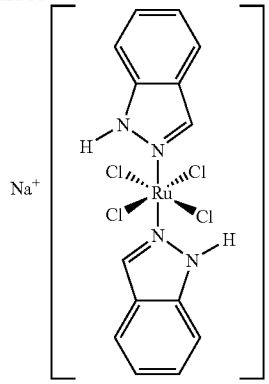

In this method, due to the limited solubility of the tetramethylammoniumchloride salt, in the second step high volumes of solvent are necessary. The efficiency of the process is low. There is need for improved alternative synthesis process.

SUMMARY OF THE INVENTION

This invention provides an efficient and convenient method for providing an alkali metal salt of trans-[tetrachlorobis(1H-indazole)ruthenate (III)].

Specifically, the present invention provides a method of making the compound M-trans-[tetrachlorobis(1H-indazole)ruthenate (III)], wherein M is an alkali metal cation, said method comprising the steps of: (1) reacting, in an aqueous solution or a mixture of water and a first organic solvent which is water soluble, indazolium trans-[tetrachlorobis(1H-indazole)ruthenate (III)] with an inorganic salt of said alkali metal cation M, to form the compound M-trans-[tetrachlorobis(1H-indazole)ruthenate (III)] and an inorganic salt of indazole; and (2) extracting said indazole from said M-trans-[tetrachlorobis(1H-indazole)ruthenate (III)] with a second organic solvent which is not substantially water soluble.

The foregoing and other advantages and features of the invention, and the manner in which the same are accomplished, will become more readily apparent upon consideration of the following detailed description of the invention taken in conjunction with the accompanying examples, which illustrate exemplary embodiments.

DETAILED DESCRIPTION OF THE INVENTION

A method is provided for making the compound M-trans-[tetrachlorobis(1H-indazole)ruthenate (III)], wherein M is an alkali metal cation. Generally, the method comprises the steps of reacting, in an aqueous solution optionally in admixture with a first organic solvent which is water soluble, indazolium trans-[tetrachlorobis(1H-indazole)ruthenate (III)] with an inorganic salt of said alkali metal cation M, to form the compound M-trans-[tetrachlorobis(1H-indazole)ruthenate (III)] and an inorganic salt of indazole; and removing said indazole from said M-trans-[tetrachlorobis(1H-indazole)ruthenate (III)] by extraction with a second organic solvent which is not substantially water soluble.

Indazolium trans-[tetrachlorobis(1H-indazole)ruthenate (III)] is a known compound disclosed in, e.g., U.S. Pat. No. 4,843,069, PCT Publication No. WO 9736595, and US Application Publication No. 2005032801. For example, it may be obtained by reacting ruthenium chloride with excess indazole to give indazolium-trans-[tetrachlorobis(1H-indazole)ruthenate (III)].

Thus, in the method of the present invention, indazolium-trans-[tetrachlorobis(1H-indazole)ruthenate (III)] is reacted with an inorganic salt of an alkali metal cation M in an aqueous solution optionally in admixture with a water soluble organic solvent. For example, the compound indazolium-trans-[tetrachlorobis(1H-indazole)ruthenate (III)] can be first dissolved in an aqueous solution optionally in admixture with a water soluble organic solvent, and then the inorganic salt of an alkali metal cation M is added thereto. Alternatively, the compound indazolium-trans-[tetrachlorobis(1H-indazole)ruthenate (III)] and the inorganic salt of an alkali metal cation M, can be mixed and dissolved in an aqueous solution optionally in admixture with a water soluble organic solvent. Also alternatively, the inorganic salt of an alkali metal cation M can be first dissolved in an aqueous solution optionally in admixture with a water soluble organic solvent, and the resultant mixture is used to dissolve the compound indazolium-trans-[tetrachlorobis(1H-indazole)ruthenate (III)].

Preferably, the compound indazolium-trans-[tetrachlorobis(1H-indazole)ruthenate (III)] and the inorganic salt of an alkali metal cation M are mixed and dissolved in water, preferably in a mixture of water and a water soluble organic solvent. The water soluble organic solvent preferably is fully mixable with water without a phase separation. The mixture of an aqueous solution or water with the water soluble organic solvent must be able to dissolve the compound indazolium-trans-[tetrachlorobis(1H-indazole)ruthenate (III)]. In addition, the organic solvent should not substantially coordinate to ruthenium. Examples of suitable water soluble organic solvent include, but are not limited to, THF, acetone, dioxane, water soluble alcohol (e.g., methanol, ethanol, propanol, 2-propanol), acetonitril, pyridine, DMF, DMSO, and the like, and mixtures thereof. Preferably, THF and/or acetone are used. When an aqueous solution or water is admixed with a water soluble organic solvent, the volume to volume ratio between the aqueous solution or water and the solvent (v/v) can be, e.g., from about 50:1 to about 1:10, about 10:1 to about 1:5, and preferably about 5:1 to about 1:1. The ratio between the compound indazolium-trans-[tetrachlorobis(1H-indazole)ruthenate (III)] and the total liquid (aqueous solution optionally in admixture with an organic solvent) (w/v) can be, e.g., from about 1:10 to about 1:500, preferably about 1:90-1:200.

The alkali metal cation M can be any alkali metal ion, but preferably is sodium or potassium cation. The inorganic salt can be a salt of sulphate, acetate, hydrogen carbonate, phosphate, hydrogenphosphate, dihydrogenphosphate, fomiate, and the like. Preferable, the inorganic salt does not have a substantial affinity so as to coordinate to ruthenium. In a preferred embodiment, the inorganic salt is sodium dihydrogenphosphate ($NaH_2PO_4$) or a solvate thereof.

The molar ratio between the compound indazolium-trans-[tetrachlorobis(1H-indazole)ruthenate (III)] and the inorganic salt can be, for example, from about 1:1 to about 1:50, preferably from about 1:1 to about 1:5, and from about 1:1 to about 1:1.1 or 1:1.2.

Once the reaction between the compound indazolium-trans-[tetrachlorobis(1H-indazole)ruthenate (III)] and the inorganic salt is complete, the indazole is removed by extraction with another organic solvent which is not substantially water soluble (the "indazole extraction solvent"). That is, this indazole extraction solvent is not substantially miscible with water, and indazole is substantially soluble in this organic solvent. In addition, the water insoluble organic solvent must also be able to form a separate phase from the water soluble organic solvent used in the reaction described above. Examples of the indazole extraction solvent include, but are not limited to, halogenated hydrocarbons such as tetrachloromethane, chloroforme, dichloromethane, and dichloroethane; aliphatic hydrocarbons such as n-hexane, n-pentane, n-heptane, petrolether, cyclohexane, cyclopentane; aromatics such as benzene and toluene; and ethers such as diethylether, diisopropylether and MTBE. Halogenated hydrocarbons, such as dichloromethane, are preferred.

Because indazole is soluble in this water insoluble organic solvent, the water insoluble organic solvent is used to extract indazole from the water soluble or aqueous phase. During the extraction, the water insoluble phase containing indazole is discarded. The amount of the water insoluble organic solvent required can vary depending on the amount of indazole to be extracted and the volume of the reaction mixture described above, as the skilled artisan would understand. Extraction for three or four times at a w/w ratio between the organic water insoluble solvent and the compound indazolium-trans-[tetrachlorobis(1H-indazole)ruthenate (III)] of e.g., 1000:1 to 1:1, preferably 600:1 to about 10:1 can achieve a sufficient purity in the final result of the aqueous phase.

Optionally, after the extraction of indazole, the alkali metal salt, M-trans-[tetrachlorobis(1H-indazole)ruthenate (III)]-containing aqueous liquid is further processed. In one embodiment, the M-trans-[tetrachlorobis(1H-indazole)ruthenate (III)]-containing aqueous liquid is extracted with an organic polar solvent which is not substantial water soluble, but in which the alkali metal salt of the ruthenium complex is substantially soluble ("ruthenium complex extracting solvent"). An example of such solvent is ethyl acetate. The amount of the polar water insoluble organic solvent required can vary depending on the alkali metal salt of the ruthenium complex, as the skilled artisan would understand. For example, a w/v ratio between M-trans-[tetrachlorobis(1H-indazole)ruthenate (III)] and the organic solvent can be from about 1:10 to about 1:1000, preferably about 1:100 to about 1:500. The extraction step can be repeated several times for best result. Preferably, before this extraction step, the M-trans-[tetrachlorobis(1H-indazole)ruthenate (III)]-containing aqueous liquid is saturated with a neutral inorganic salt of the alkali metal cation M so as to reduce the solubility of the M-trans-[tetrachlorobis(1H-indazole)ruthenate (III)] in the aqueous liquid and to force it into the organic phase during extraction. Suitable salts include, but are not limited to, chloride salt (e.g., NaCl, KCl) and sulphate salt ($Na_2SO_4$), and preferably NaCl is used when M is sodium.

After the extraction, the M-trans-[tetrachlorobis(1H-indazole)ruthenate (III)] can be precipitated from the organic phase, i.e., the ruthenium complex extracting solvent by mixing with another less polar organic solvent ("precipitation solvent"). Examples of such less polar organic solvent include, but are not limited to, ethers such as ethyl ether (e.g., diethyl ether), methyl tert-butyl ether, petrol ether; and hydrocarbons such as n-pentane, n-hexane, and cyclohaxane; and combinations thereof. The amount of the less polar organic precipitation solvent required can vary depending on the amount of alkali metal salt of the ruthenium complex and the volume of the polar organic phase, i.e., the ruthenium complex extracting solvent, as the skilled artisan would understand. For example, a w/v ratio between M-trans-[tetrachlorobis(1H-indazole)ruthenate (III)] and the precipitation solvent can be from about 1:10 to about 1:1000, preferably about 1:100 to about 1:500. Preferably, the precipitation/crystallization step is performed at from about 1° C. to about 25° C., preferably from about 3° C. to about 10° C., more preferably at about 5° C. The precipitates/crystalline M-trans-[tetrachlorobis(1H-indazole)ruthenate (III)] can be filtered and washed with the same or different precipitation solvent. Optionally, the precipitates/crystalline M-trans-[tetrachlorobis(1H-indazole)ruthenate (III)] can be redissolve in water and lyophilized.

EXAMPLE

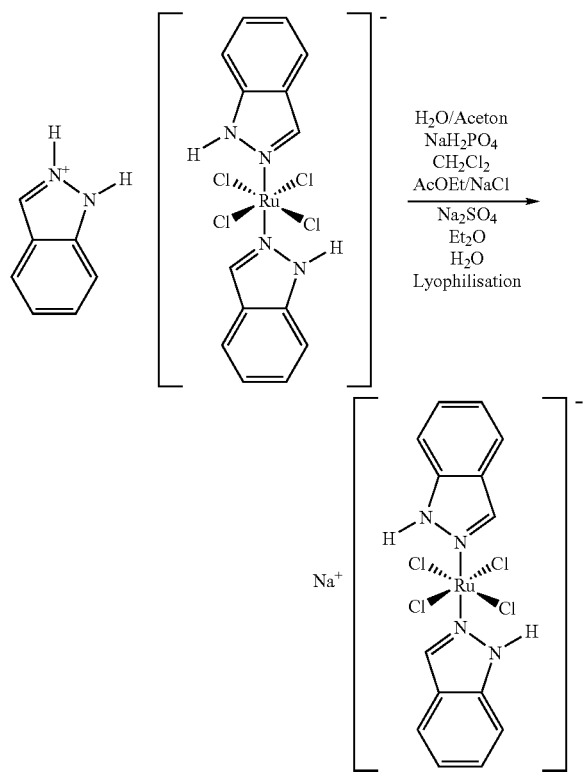

343 g (573 mMol) of indazolium trans-[tetrachlorobis(1H-indazole)ruthenate (III)] was dissolved in a mixture of 411 g (2.98 Mol) $NaH_2PO_4.H_2O$ and 23 liters of water and 8.6 liters of acetone. The mixture was stirred until a clear solution is obtained, and was extracted with 3×34 liters of $CH_2Cl_2$, and the $CH_2Cl_2$-phase is discarded. The aqueous phase was extracted with 34 liters of ethyl acetate (100 parts) under saturation with NaCl (~3.4 kg). The ethyl acetate phase was dried over $Na_2SO_4$ (~3.4 kg), and the product was precipitated by addition of 68.5 liters of diethyl ether and stirring for 3 hours at 5° C. The precipitate was filtered and washed with 3×1.7 liters of diethyl ether. After redissolution in 17 liters of water, the product was lyophilized until the loss of weight was <0.1%/4 h. The yield was 118 g orange to brown solid (41% of th.).

For further purification, 112 g (223 mMol) of the above product was suspended in 1100 ml ethyl acetate, and the suspension was stirred for 30 minutes at room temperature. The product was filtered and washed twice with 100 ml ethyl acetate. After redissolution in 4200 ml water, the product was lyophilized until loss of weight is <0.1%/4 h. 103 g orange to brown solid (93% of th.) was yielded.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be apparent that certain changes and modifications may be practiced within the scope of the appended claims.

What is claimed is:

1. A method of making the compound M[tetrachlorobis(1H-indazole)ruthenate (III)], wherein M is an alkali metal cation, comprising the steps of,
  reacting, in an aqueous solution or a mixture of an aqueous solution and a first organic solvent which is water soluble, indazolium trans-[tetrachlorobis(1H-indazole)ruthenate (III)] with an inorganic salt of said alkali metal cation M, to form the compound M[tetrachlorobis(1H-indazole)ruthenate (III)] and an inorganic salt of indazole; and
  removing said indazole from said M[tetrachlorobis(1H-indazole)ruthenate (III)] by extraction with a second organic solvent which is not substantially water soluble.

2. A method of making the compound M[tetrachlorobis(1H-indazole)ruthenate (III)], wherein M is an alkali metal cation, comprising:
  dissolving indazolium trans-[tetrachlorobis(1H-indazole)ruthenate (III)] in an aqueous solution or a mixture of an aqueous solution and a first organic solvent which is water soluble;
  reacting said indazolium trans-[tetrachlorobis(1H-indazole)ruthenate (III)] with an inorganic salt of said alkali metal cation M to form the compound M[tetrachlorobis(1H-indazole)ruthenate (III)] and an inorganic salt of indazole; and
  extracting said indazole from said M[tetrachlorobis(1H-indazole)ruthenate (III)] with a second organic solvent which is not substantially water soluble.

3. The method of claim 2, wherein M is sodium, and said inorganic salt of said alkali metal cation M is sodium dihydrogenphosphate.

4. A method of making the compound sodium trans [tetrachlorobis(1H-indazole)ruthenate (III)], comprising the steps of,
  reacting, in an aqueous solution optionally in admixture with a first organic solvent which is water soluble, indazolium trans-[tetrachlorobis(1H-indazole)ruthenate (III)] with an inorganic salt of sodium, to form the compound sodium trans [tetrachlorobis(1H-indazole)ruthenate (III)] and an inorganic salt of indazole; and
  removing said indazole from said sodium trans [tetrachlorobis(1H-indazole)ruthenate (III)] by extraction with a second organic solvent which is not substantially water soluble.

5. A method of making the compound sodium trans [tetrachlorobis(1H-indazole)ruthenate (III)], comprising the steps of,
  (1) reacting, in an aqueous solution optionally in admixture with a first organic solvent chosen from acetone or THF or a mixture thereof, indazolium trans-[tetrachlorobis(1H-indazole)ruthenate (III)] with $NaH_2PO_4$, to form the compound sodium trans [tetrachlorobis(1H-indazole)ruthenate (III)] and a dihydrophosphate salt of indazole;
  (2) removing said indazole from said sodium trans [tetrachlorobis(1H-indazole)ruthenate (III)] by extraction with $CH_2Cl_2$;
  (3) extracting the sodium trans [tetrachlorobis(1H-indazole)ruthenate (III)] resulted from step (2) with ethyl acetate under saturation with NaCl; and
  (4) precipitating the sodium trans [tetrachlorobis(1H-indazole)ruthenate (III)] from step (3) by addition of diethyl ether.

* * * * *